United States Patent
Emsky

(10) Patent No.: US 7,201,729 B2
(45) Date of Patent: Apr. 10, 2007

(54) METHOD AND APPARATUS FOR THERAPEUTIC TREATMENT OF BACK PAIN

(75) Inventor: Timothy R. Emsky, Prince George (CA)

(73) Assignee: Cert Health Sciences, LLC, Baltimore, MD (US)

( * ) Notice: Subject to any disclaimer, the term of this patent is extended or adjusted under 35 U.S.C. 154(b) by 166 days.

(21) Appl. No.: 10/737,098

(22) Filed: Dec. 16, 2003

(65) Prior Publication Data

US 2004/0171974 A1 Sep. 2, 2004

Related U.S. Application Data

(60) Provisional application No. 60/433,664, filed on Dec. 16, 2002.

(51) Int. Cl.
*A61F 5/00* (2006.01)

(52) U.S. Cl. .......................... 602/33; 606/240; 606/242; 128/845

(58) Field of Classification Search ................ 606/240, 606/241, 242, 243, 244, 245; 602/32, 33, 602/36; 128/845; 5/600, 607, 610–614, 5/617, 619, 650, 652, 621, 624, 632, 657, 5/658; 601/23–26
See application file for complete search history.

(56) References Cited

U.S. PATENT DOCUMENTS

| | | | |
|---|---|---|---|
| 4,387,888 A | 6/1983 | Marinakis | |
| RE32,791 E | 11/1988 | Saunders | |
| 4,995,378 A | 2/1991 | Dyer et al. | |
| 5,115,802 A | 5/1992 | Dyer | |
| 5,141,483 A * | 8/1992 | Smith | 606/243 |
| 5,192,306 A | 3/1993 | Scott et al. | |
| 5,208,928 A | 5/1993 | Kuck et al. | |
| 5,308,359 A | 5/1994 | Lossing | |
| 5,362,302 A | 11/1994 | Jensen et al. | |
| 5,369,825 A | 12/1994 | Reesby | |
| 5,730,706 A * | 3/1998 | Garnies | 606/241 |
| 5,794,286 A | 8/1998 | Scott et al. | |

(Continued)

FOREIGN PATENT DOCUMENTS

FR 2630910 11/1998

(Continued)

OTHER PUBLICATIONS

Chrirotables.com; http://www.chirotables.com/newtables/hill.htm; Hill Chiropractic tables.

(Continued)

*Primary Examiner*—Quang D. Thanh
(74) *Attorney, Agent, or Firm*—Whiteford, Taylor & Preston LLP

(57) ABSTRACT

A therapeutic table construction which isolates a first portion of the patient's body to a fixed table portion and a second portion of the patient's body to a moveable table portion, and applies a distraction force to the moveable portion of the patient's body while positioning the portion of the patient's spine that is to be treated at an angle so as to isolate the portion of the patient's spine which receives the distraction force.

40 Claims, 12 Drawing Sheets

U.S. PATENT DOCUMENTS

| | | | |
|---|---|---|---|
| 5,860,899 A * | 1/1999 | Rassman | 606/242 |
| 6,039,737 A | 3/2000 | Dyer | |
| 6,152,950 A | 11/2000 | Shealy et al. | |
| 6,202,230 B1 | 3/2001 | Borders | |
| 6,277,141 B1 * | 8/2001 | Lake | 606/243 |
| 6,428,497 B1 * | 8/2002 | Crouch | 602/32 |
| 6,638,299 B2 | 10/2003 | Cox | |
| 6,671,905 B2 | 1/2004 | Bartlett et al. | |
| 6,874,181 B1 | 4/2005 | Connolly et al. | |
| 6,874,182 B2 | 4/2005 | L'Hegarat et al. | |
| 2002/0138905 A1 | 10/2002 | Bartlett et al. | |
| 2003/0088919 A1 | 5/2003 | Lin | |
| 2003/0115674 A1 | 6/2003 | Heimbrock et al. | |

FOREIGN PATENT DOCUMENTS

| | | |
|---|---|---|
| WO | WO9003158 | 4/1990 |

OTHER PUBLICATIONS

Chirotables.com; http://www.chirotables.com/newtables/zflexion.htm; Zenith Flexion Tables, Fexion/Distraction Table Model 95, Flexion/D. . .

* cited by examiner

FIGURE 11

Patients
Patient, Joe — 141
First Name: Joe
Last Name: Patient
Patient Address: 123 Anywhere Street
City: Big City, Big State, 19991
Phone #: (866) 990-4444    DOB: 01/01/2001    Gender: Male

140

Patient ID: 1234
Weight: 300 (lb) (136.1 kg)
Post Surgical: No
Date if TX: 01/01/2001
Symptom Duration: 3 months Lumbar
☑ Herniation  ☐ DDD  ☐ Facet Syn.  ☐ L1-L2  ☐ L2-L3  ☐ L3-L4  ☑ L4-L5  ☐ L5-L6

Cervical
☐ Herniation  ☐ DDD  ☐ Facet Syn.  ☐ C1-C2  ☐ C2-C3  ☐ C3-C4  ☐ C5-C6  ☐ C6-C7

| 1 | 2 | 3 | 4 | 5 | 6 | 7 | 8 | 9 | 0 | Back |
| Q | W | E | R | T | Y | U | I | O | P |  |
| Caps | A | S | D | F | G | H | J | K | L | . |
| Delete | Z | X | C | V | B | N | M | , | Enter |  |
| Space |

Action
Save    Main Menu

METHOD AND APPARATUS FOR THERAPEUTIC TREATMENT OF BACK PAIN

CROSS REFERENCE TO RELATED APPLICATION

This application is based upon and claims benefit of copending and co-owned U.S. Provisional Patent Application Ser. No. 60/433,664 entitled "Method and Apparatus for Therapeutic Treatment of Back Pain", filed with the U.S. Patent and Trademark Office on Dec. 16, 2002, by the inventor herein, the specification of which is incorporated herein by reference.

FIELD OF THE INVENTION

The present invention relates to methods and apparatus for the treatment of back pain, and more particularly to a method and apparatus for treating lower back pain caused by herniated, bulging, or degenerative disks, facet syndrome, failed back surgery, or other physiological disorders of the spine.

BACKGROUND OF THE INVENTION

Intervertebral disk injuries and degeneration have long been a contributing factor to lost employee time for a large number of companies. In fact, it is estimated that 80% of the population will experience severe back pain during their life, while millions live with chronic back pain every day. Excessive loading of the spine through changes in a person's lifestyle, extended periods of sitting while driving or sitting at a desk, and many other factors all may cause premature degeneration of intervertebral discs and repeated injury of the disc annulus.

Often times, treatment of such injuries in an effort to return a person to their livelihood has included conservative treatment modalities that have provided at best only temporary relief, and as a last resort, invasive surgery that ordinarily carries an associated risk of paralysis.

Moreover, despite efforts to alleviate back pain symptoms, severely damaged discs seldom heal. Nutrition in the avascular disc depends on osmotic diffusion of collagen precursors (e.g., proline), nutrients, and oxygen through direct channels in the annulus (30%), and the hyaline end plate in the vertebrae above and below the disc (70%). It is estimated that the cycle of proline uptake and renewal in the normal disc (necessary for collagen synthesis and repair) takes approximately 500 days. This inherently slow cycle is additionally compromised in the deranged disc. By lowering intradiscal pressures, properly applied spinal disc decompression therapy (i.e., unloading due to distraction and positioning) would greatly facilitate this process and accelerate healing in the disc segment.

Mechanical traction has been used in the past in an attempt to alleviate the pain associated with damaged disc structures, but such methods have provided highly inconsistent results. Such mechanical traction involves the application of a distracting force to either realign a structural abnormality or to relieve excessive intradiscal pressures. Successful mechanical traction can alleviate the pain symptoms associated with such disorders. However, prior known methods and apparatus for providing mechanical traction apply the distraction force to the entire spine, thus "treating" areas of the spine that do not exhibit such disorders. Such inefficient application of force to the entire spine structure carries an increased risk of mechanical traction side effects to normal areas of the spine, such as muscle strain and spasm. It would therefore be advantageous to provide a method and apparatus for applying a distracting force to a localized area of the spine that requires treatment, as opposed to the entire spinal column.

Moreover, prior known methods and apparatus for providing mechanical traction ordinarily apply harnesses to the patient's upper body portion and pelvis, and pull the pelvic harness so as to apply a traction force to the patient's spine. Such force application ordinarily requires that a significant amount of frictional force between the patient's body and the table surface be overcome, as application of the distraction forces will require relative movement between the patient's body and the table surface. Overcoming such frictional forces may cause the forces transferred from the pulling apparatus to the patient's spine to vary from a uniform, linear force application, in turn increasing the risk of side effects such as muscle spasm and patient discomfort. It would therefore also be advantageous to provide a method and apparatus for applying a distracting force to a patient's spine while minimizing the occurrence of non-uniform force application.

Still further, the patient receiving the mechanical traction treatment often has no control over the treatment process. This causes anxiety in the patient, in turn often causing the patient to tense the muscles in his or her back, which in turn can lead to increased risk of muscle spasm. It would therefore also be advantageous to provide a method and apparatus for applying a distracting force while enabling the patient to maintain a measure of control over the treatment process.

SUMMARY OF THE INVENTION

The present invention provides a method and apparatus for applying a uniform, linear distracting force to a localized area of the spine, enables effective distraction treatment with application of a lower distraction force than has typically been required, and preferably enables a patient undergoing treatment to maintain the ability to terminate the treatment without requiring interaction from medical personnel.

The apparatus of the instant invention comprises a therapeutic table construction which, in a first preferred embodiment, isolates the top portion of the patient's body with respect to a fixed upper portion of the table, isolates the bottom portion of the patient's body with respect to a moveable lower portion of the table, and applies a distraction force to the bottom portion of the patient's body while positioning the patient's pelvis at an angle so as to isolate the portion of the patient's spine which receives the distraction force. By accurately tilting the pelvis during distraction, specific spinal segments are targeted to enable the precise treatment of a particularly identified pathology. This feature eliminates the unnecessary treatment of additional spinal segments, and any resulting side effects.

In a second preferred embodiment, the apparatus of the instant invention comprises a therapeutic table construction which isolates a patient's head with respect to a moveable head support portion of the table, and isolates the torso portion of the patient's body with respect to a fixed upper portion of the table, and applies a distraction force to the cervical portion of the patient's spine while positioning the patient's head and neck at an angle so as to isolate the portion of the patient's cervical spine which receives the distraction force. Once again, by accurately tilting the patient's head and neck during distraction, specific cervical spinal segments are targeted to enable the precise treatment of a particularly identified pathology, which feature again eliminates the unnecessary treatment of additional spinal segments, and any resulting side effects.

Prior distraction devices have utilized nylon harnesses and straps to secure the patient's pelvis and upper body to the energy source. In these circumstances, energy is absorbed in the several square feet of nylon fabric and several linear yards of nylon strapping. In addition, energy is dispersed throughout the soft tissues between the harness and the skeletal structure. The present invention, however, reduces energy loss and absorption by, in a first embodiment, securing the pelvis directly, and in a second embodiment, securing the base portion of a patient's skull directly. The elimination of energy loss and absorption allows for a much lower distraction force, which subsequently reduces side effects such as muscle spasm and patient discomfort.

An infrared heating pad is also preferably integrated with the apparatus that provides radiating heat at an effective depth of three centimeters to paravertebral tissues during distraction. This warming of tissues provides a more relaxed distraction of the spine, and in turn reduces the incidence of muscle spasm. To further a patient's relaxation during the therapeutic process, a CD sound system with wireless headphones is preferably integrated with the apparatus to provide the patient with relaxation music throughout the therapy session.

The apparatus also provides both mechanical and electrical, patient-operable, system termination devices. By activation of either of those devices, the patient can halt application of force to his or her spine at any time. Thus, treatment is able to proceed without medical personnel in the immediate vicinity of the apparatus. This unsupervised treatment allows the device to be placed in a quiet and darkened area to even further promote relaxation, and perhaps even sleep, for the patient.

The operation of the therapeutic table is controlled by computer software running on a computer processor that is integrated with a control unit for the table. To reduce operator error and to maintain treatment consistency, the device software defines the majority of the treatment parameters for the operator based on a defined protocol, or will prompt the operator with a recommended value, which is based on individual patient data. At the outset of a treatment session, personal data about the patient is input to the computer software, and based upon the patient's individual characteristics, an individualized patient treatment protocol is determined and executed by the software. In order to reduce the incidence of human error, the table operator is preferably prompted with a series of default values for each treatment parameter that is to be entered prior to initiating the treatment regimen. The patient data that is input to the software preferably includes the patient's personal identification data, known pathology related to the treatment, history of the patient's condition, and previous alternate treatment undergone for this pathology. The software uses the data stored in an individual patient's data file, such as body weight, to customize the treatment for the specific patient. The software calculates every parameter of the treatment, other than the tilt angle of the pelvis or head support. The operator of the device has the ability to override the maximum tension applied by the table to ensure patient-specific tailoring of the treatment. A measure of each patient's pain, disability, and symptoms are collected and attached to the treatment record to track individual treatment efficacy. Each treatment becomes a permanent record stored in a database associated with the processor of the control unit.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 11 is an exemplary patient data screen for use with the method and system of the instant invention.

FIG. 12 is an exemplary treatment control screen for use with the method and system of the instant invention.

FIG. 13 is an exemplary report control screen for use with the method and system of the instant invention.

DETAILED DESCRIPTION OF THE PREFERRED EMBODIMENT

Figure 1:
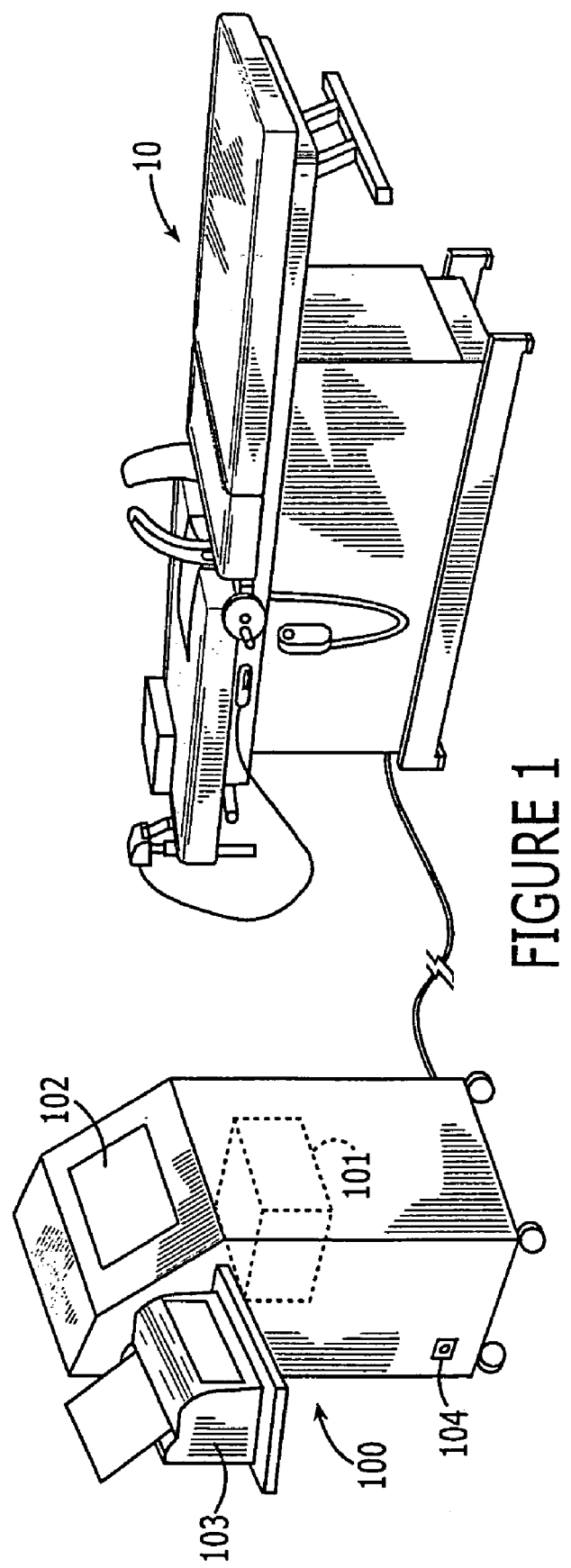
FIG. 1 is a perspective view of a system for the therapeutic treatment of back pain according to a first preferred embodiment of the instant invention.

The invention summarized above and defined by the enumerated claims may be better understood by referring to the following description, which should be read in conjunction with the accompanying drawings in which like reference numerals are used for like parts. This description of an embodiment, set out below to enable one to build and use an implementation of the invention, is not intended to limit the enumerated claims, but to serve as a particular example thereof. Those skilled in the art should appreciate that they may readily use the conception and specific embodiment disclosed as a basis for modifying or designing other methods and systems for carrying out the same purposes of the present invention. Those skilled in the art should also realize that such equivalent assemblies do not depart from the spirit and scope of the invention in its broadest form.

A preferred embodiment of the apparatus of the instant invention is initially described with reference to FIG. 1, in which a decompression table 10 suitable for applying a distraction force to a targeted portion of a patient's spine is provided in communication with a control unit 100.

Figure 2A:
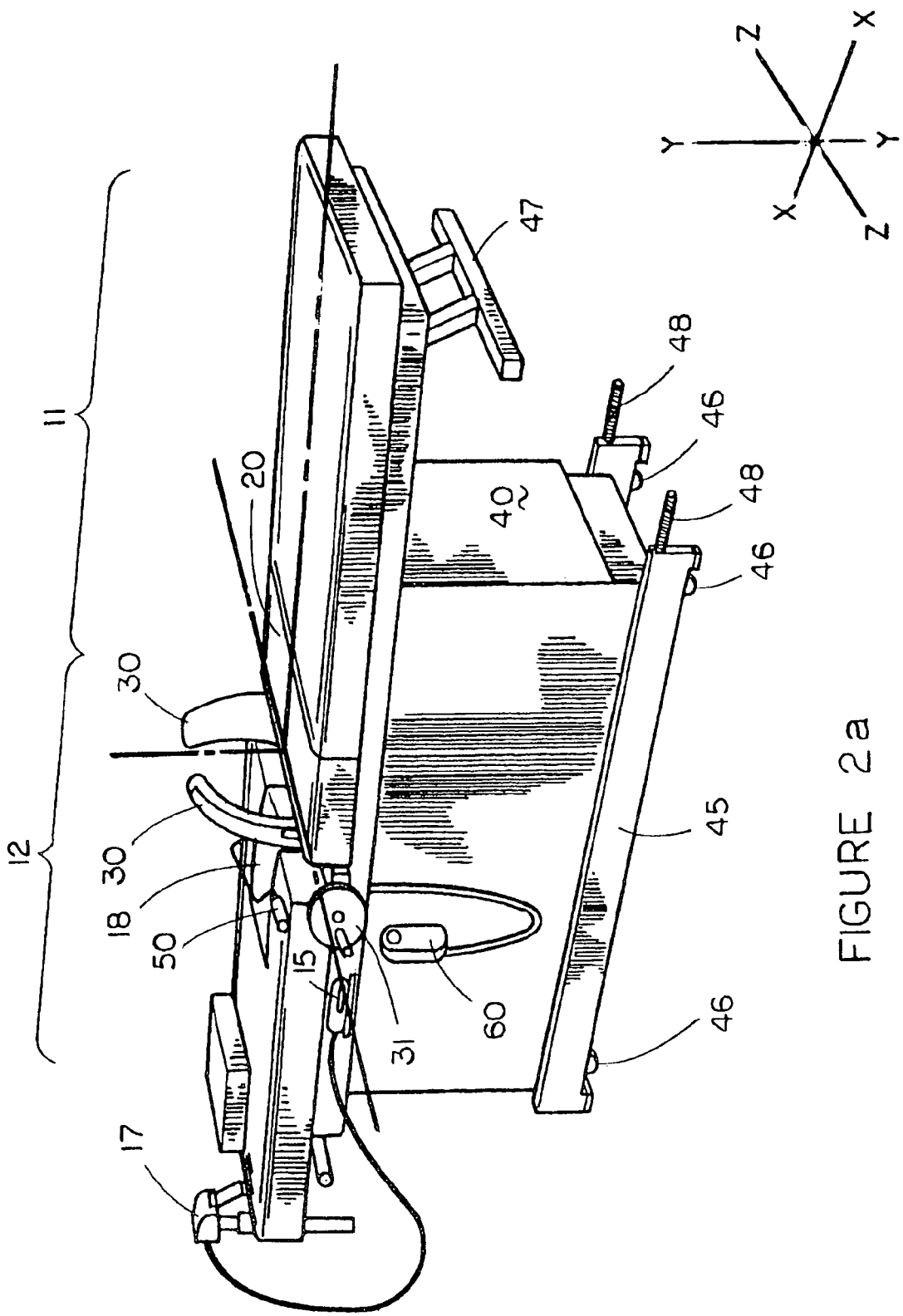
FIG. 2a is a left side perspective view of a decompression table according to the embodiment of FIG. 1.
Figure 2B:
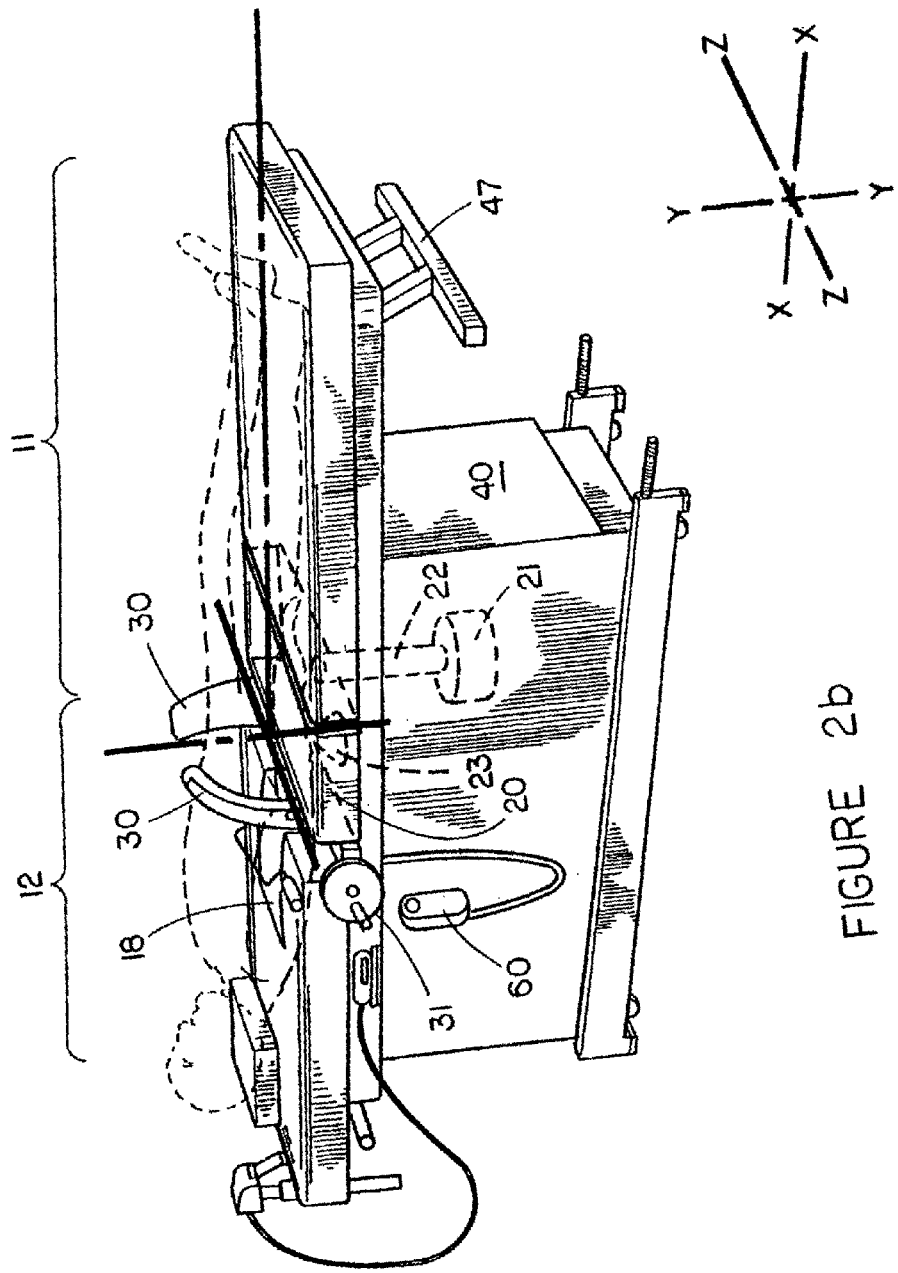
FIG. 2b is a left side perspective view of the decompression table of FIG. 2a showing in phantom the position of a patient lying supine on the decompression table.

As shown more particularly in the left side perspective view of FIG. 2, in a first preferred embodiment of the invention, decompression table 10 comprises a powered, moveable lower table section 11 and a fixed upper section 12. Lower table section 11 includes a tilting pelvic support 20 that allows tilting of the pelvis during distraction. A pair of pelvic restraint horns 30 is provided between the upper section and the tilting pelvic support 20 which are moveable toward and away from one another to adjustably grip against the sides of a patient's body, just above the superior iliac crests, when the patient is positioned on the decompression table 10. A hand crank 31 is provided to allow an operator to manually adjust the position between facing pelvic restraint horns 30.

During use, lower table section 11 is translated away from fixed upper table section 12 so as to provide a distraction force to the patient's spine, and is translated back towards upper table section 12 to reduce and/or remove such distraction force. To enable such operation, lower table section 11 is supported on a sliding rail assembly that is attached to the actuator arm of an electric motor having a linear actuator (not shown). Operation of the motor causes the actuator arm to extend and retract, in turn moving lower table section 11 away from and toward upper table section 12, respectively. Such drive elements per se are well known in the art.

Tilting pelvic support 20 is moveable preferably in five degree increments, such that it may realize an angle of 0°, 5°, 10°, 15°, 20°, and 25°, and thus tilt the patient's pelvis to such degree during distraction. The settings required for the angle of the pelvis during the distraction are entered into control unit 20 by the system operator at the start of the treatment session, as explained in greater detail below. The particular angle that is to be implemented is determined by the level of the spine where distraction is intended to occur. While correlation of particular angles with spinal sections is believed a matter of medical skill, it has been found that the following protocol is particularly useful with the first preferred embodiment described herein. A setting of 0° tilt angle is useful for applying a distraction force at L5-S1. A setting of 5° tilt angle is useful for simultaneously applying a distraction force at L5-S1 and at L4-L5. A setting of 10° tilt angle is useful for applying a distraction force at L4-L5. A setting of 15° tilt angle is useful for simultaneously applying a distraction force at L4-L5 and at L3-L4. A setting of 20° tilt angle is useful for applying a distraction force at L3-L4. Lastly, a setting of 25° tilt angle is useful for applying a distraction force from L2-L3 to L1-L2. In order to achieve the desired tilt angle, a separate electro-mechanical drive 21 is mounted below pelvic support 20 having an extensible actuating arm 22 which, when extended, pivots pelvic support 20 about a pivot 23 on the underside of support 20.

Figure 3:
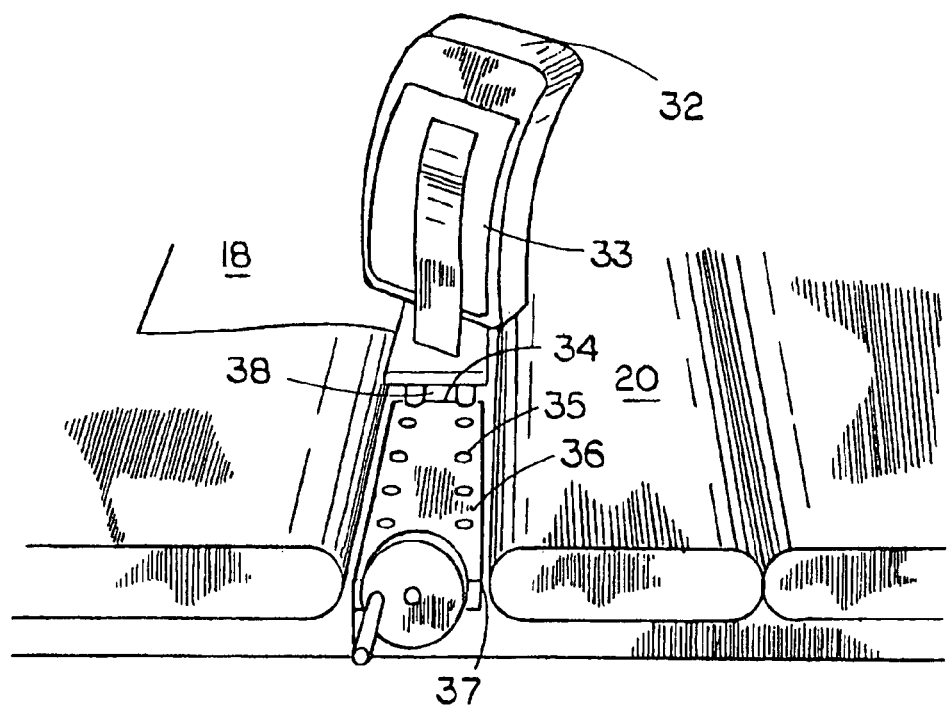
FIG. 3 is a side perspective view of a pelvic restraint system for use with the table of FIG. 2.

Pelvic restraint horns 30 are adapted to move toward and away from one another through manipulation of hand crank 31. As shown in FIG. 3, pelvic restraint horns 30 preferably include a rounded pad 32 mounted to a rigid bracket 33. Located at the bottom of bracket 33 are positioning pins 34 which are configured for insertion into pin holes 35 in slider block 36. Slider block 36 is in turn configured to ride along slide rail 37 so that facing restraint horns 30 may be moved toward and away from one another. Preferably, a plurality of sets of pin holes 35 are provided in each slider block 36 so as to enable the restraint horns to be mounted in a variety of configurations as may be required for patients of varying body sizes. Also, pins 34 and pinholes 35 are configured to allow restraint horns 30 to easily be removed from slider block 36. Thus, the pelvic restraint horns may be removed upon loading and unloading a patient onto and off of the decompression table 10. Once a patient is loaded onto the decompression table 10, restraint horns 30 are positioned in slider blocks 36 and hand crank 31 is manipulated to bring facing restraint horns 30 towards one another. Hand crank 31 is mounted to an acme screw 38 of traditional design, such that rotation of hand crank 31 causes slider blocks 36 to linearly translate toward or away from one another, depending upon the direction of rotation of hand crank 31. The restraint horns 30 and slide rail assembly are so positioned on decompression table 10 that when restraint horns 30 press against a patient's body, they are positioned immediately above the superior iliac crests on both sides of the patient's pelvis. So placed, the restraint horns 30 are then tightened against the sides of the patient's body via further manipulation of hand crank 31 to securely and comfortably hold the patient's pelvis to moveable lower table section 11. This assembly thus temporarily affixes the lower portion of the patient's body to moveable lower table section 11, and more particularly affixes the patient's pelvis to pelvic support 20.

Optionally, pelvic restraint horns 30 may be provided in varying sizes to ensure comfortable restraint of different sized patients. Moreover, pelvic restraint horns 30 are preferably angled slightly such that the padded, interior face of each pelvic restraint horn 30 is turned slightly toward the bottom of table 10 when inserted in each slider block 36 so as to better engage a patient's iliac crests and more efficiently direct a distraction force to the desired portion of the patient's spine.

It is notable that prior traction systems have utilized a belt or harness separate from a fixed table structure, which belt or harness is strapped to the patient's pelvis and pulled to apply a distraction force to the patient's spine. However, by relying on such a configuration, the forces applied to the patient's spine tend to be countered by the frictional forces between the patient's body and the table surface. This in turn complicates the force application and can cause the application of non-uniform forces to the patient's spine during the therapeutic session. Contrastingly, the decompression table of this first embodiment of the instant invention effectively affixes the patient's pelvis to a moveable section of the decompression table 10, such that relative movement between the patient's pelvis (or other body portions) and the table 10 need not occur during the application of distraction forces. This allows for greater control and uniformity in applying distraction forces than prior known apparatuses, and likewise reduces the risk of side effects typically associated with prior known spinal traction treatments.

Figure 4A:
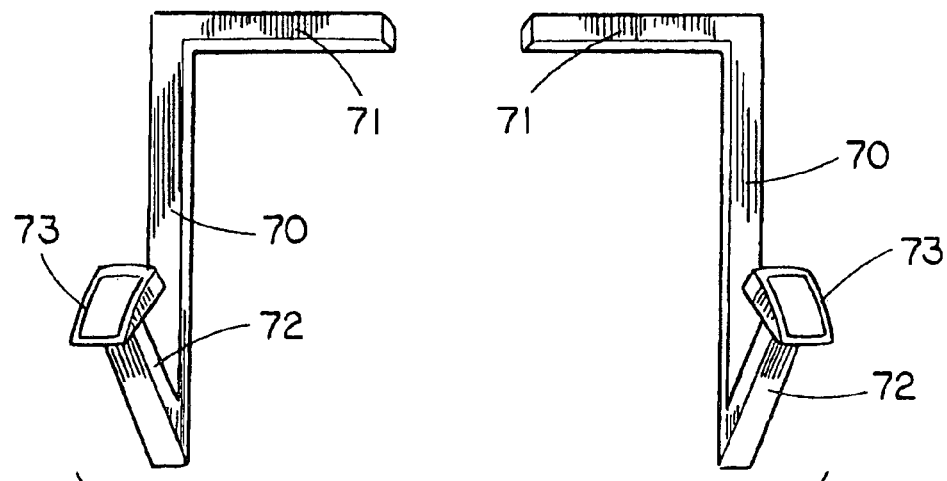
FIGS. 4a and 4b are a top and side view, respectively, of elements of a supplementary pelvic restraint for use with the table of FIG. 2.
Figure 4B:
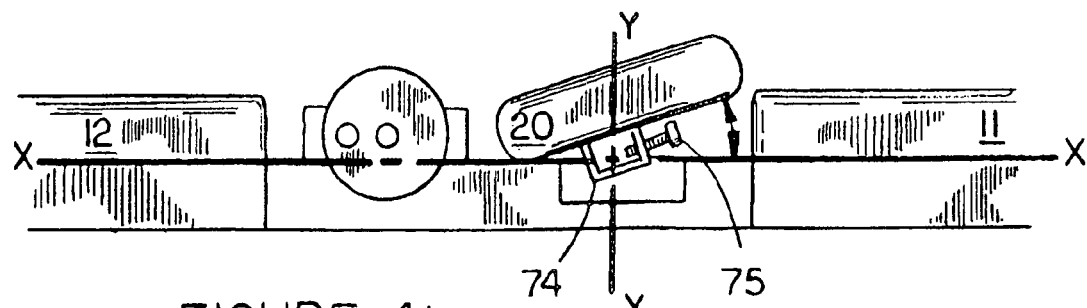

In the event that pelvic restraint horns 30 are unsuitable for a particular patient (e.g., an extremely obese patient requiring distraction treatment), a secondary restraint system for the pelvis is optionally provided for isolating the lower portion of the patient's body to lower table section 11, and more particularly for isolating the patient's pelvis to pelvic support 20. As shown in the top perspective view of FIG. 4a and the left side perspective view of FIG. 4b, such secondary restraint system preferably includes two rigid arms 70 having at one end thereof a connecting rod 71. Connecting rods 71 are configured to slide into a sleeve 74 that is affixed to tilting pelvic support 20. Thus, each arm 70 may be easily mounted to and removed from decompression table 10. A manually operable set screw 75 is optionally provided to temporarily lock each of arms 70 within sleeve 74. The opposite end of each of arms 70 preferably has a support 72, on which is mounted a buckle 73 for receiving the ends of straps attached to a pelvic belt that is strapped to the patient's pelvic region. By connecting arms 70 to pivoting pelvic support 20 through sleeve 74, both pivoting motion and horizontal motion of pivoting pelvic support 20 and lower table section 11 are translated through arms 70 and to buckles 73. Thus, the secondary restraint system moves in unison with the tilting pelvic support 20 so as to provide angled distraction forces to the pelvis in targeted portions of the patient's spine without requiring relative movement of the lower portion of the patient's body with respect to the lower table section 11, as with the pelvic horns 30 discussed above.

As shown in FIG. 2, upper table section 12 also includes a manual emergency release lever 15 placed in easy reach of a patient lying on decompression table 10, and which may be operated by the patient to activate a mechanical safety release which will disengage an upper body restraint (not shown) attached to mechanical buckle 17. Release lever 15 is connected to mechanical buckle 17 via a cable, such that operation of release lever 15 pulls the cable and likewise immediately releases the upper harness from decompression table 10 and eliminates all force application to the patient. Likewise, a patient hand-held electrical switch 50 is provided which, when activated, signals the control software to immediately discontinue the treatment session, and eliminates the application of force under a controlled rate of speed. This controlled elimination of force helps to minimize the occurrence of muscle spasm. Hand-held switch 50 is configured to be held by the patient during treatment or clipped to the patient's clothing. Thus, when lying on table 10, a patient is assured that if the treatment applies forces which are too excessive or uncomfortable for the patient to bear, the patient may simply terminate the application of the distraction forces by either releasing the upper body restraint system from fixed upper table portion 12 or terminating movement of lower table section 11.

Figure 5:
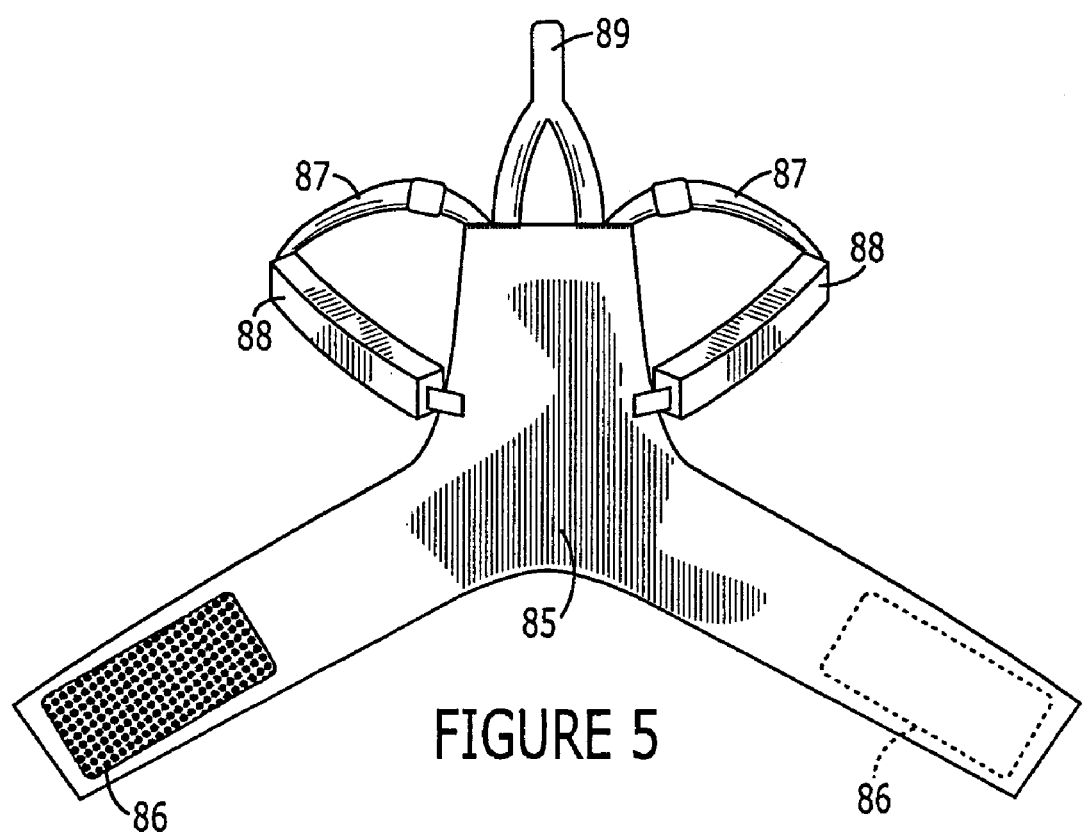
FIG. 5 is a top view of an upper body restraint system.

As shown in the top view of FIG. 5, a patient may be secured to fixed upper table portion 12 via an upper trunk stabilization system which preferably comprises a fabric harness 85 generally in the shape of an inverted "Y." Preferably, harness 85 is constructed of nylon fabric having an integral foam padding for comfort. The lower, outwardly extending arms of the harness 85 are configured to capture a patient's ribcage under the lower margin, and are preferably provided a hook-and-loop type fastener 86, such that when the lower, outwardly extending arms are wrapped around the patient's torso, they may be removably attached to one another to securely hold the patient. The upper branch of fabric harness 85 preferably includes two arm straps 87 configured to wrap over a patient's shoulders and under their armpits. Straps 87 are thus affixed to harness 85 at two locations so as to form a loop through which the patient's arms are inserted. Straps 87 are also preferably adjustable, via a buckle or similarly configured fastener, so as to accommodate patients of varying sizes. For added stability and comfort, foam padded axilla bolsters 88 are preferably provided at a lower end of straps 87 to help distribute the force being applied to the patient. A preferably nylon connecting strap 89 is also preferably provided at the top edge of harness 85, connecting strap 89 being configured for connection to mechanical buckle 17 to isolate the patient's upper body portion to the upper portion 12 of decompression table 10. Harness 85 may thus be released from decompression table 10 via operation of the mechanical safety release described in detail above. In use, a patient is first fitted with harness 85 prior to being placed on decompression table 10. Harness 85 is then placed through the patient's arms much like a jacket. The lower, outwardly extending arms of harness 85 are then positioned across and below the lower margin of the patient's ribcage, and then snugly secured. Once the patient is positioned on decompression table 10, the lower, outwardly extending arms are readjusted to comfortably secure the ribcage. The axilla bolsters are also adjusted using straps 87 so that they fit comfortably within the patient's armpit. Connecting strap 89 is then attached to the mechanical safety release, and any slack is removed from the strap.

In an alternate embodiment of decompression table 10, a second set of restraint horns, configured similarly to pelvic restrain horns 30, may be provided in upper table section 12 to isolate a patient's upper body portion to fixed upper table section 12, instead of a harness. Preferably, such torso restraint horns in upper table section 12 are adapted to move toward and away from one another, and thus are equipped with a manual operating mechanism like that used to adjust the position of pelvic restraint horns 30.

Figure 6A:
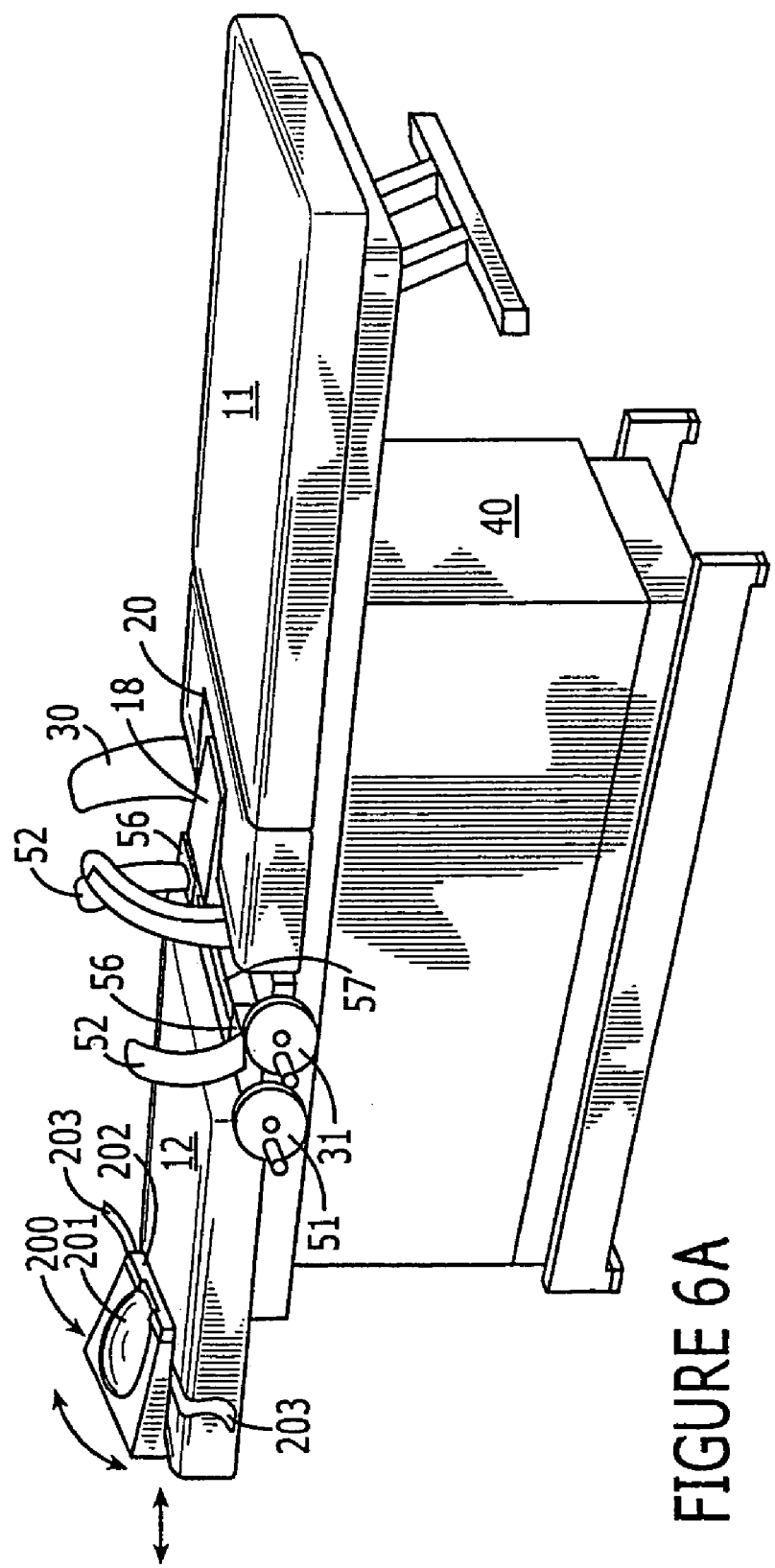
FIG. 6a is a left side perspective view of a decompression table according to a second preferred embodiment of the instant invention.
Figure 6B:
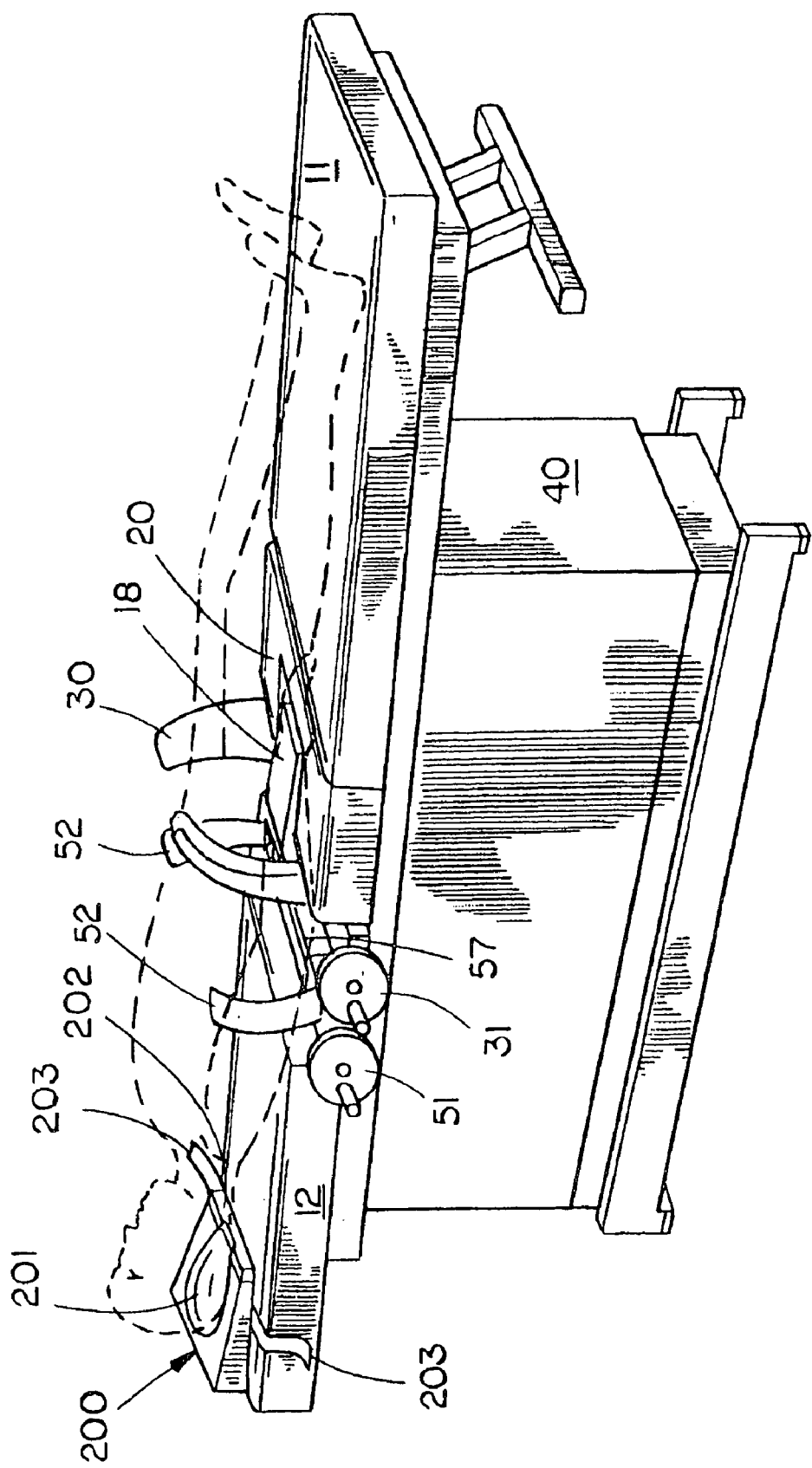
FIG. 6b is a left side perspective view of the decompression table of FIG. 6a showing in phantom the position of a patient lying supine on the decompression table.

As shown more particularly in the side perspective view of FIG. 6, the rib restraint horn assembly comprises facing rib restraint horns 52, each preferably comprised of a rounded gel pad mounted to a rigid bracket. As with pelvic restraint horns 30, located at the bottom of such bracket are positioning pins which are configured for insertion into pin holes in the top face of slider blocks 56. The bottom portion of slider blocks 56 are in turn configured to ride along a side rail 57, again preferably in the form of an acme screw, so that facing rib restraint horns 52 may be moved toward and away from one another. Preferably, a plurality of sets of pin holes are provided in each slider block 56 so as to enable the rib restraint horns 52 to be mounted in a variety of configurations as may be required for patients of varying body sizes. Also, as with pelvic restraint horns 30, such pins and pinholes are configured to allow rib restraint horns 52 to easily be removed from slider block 56. Thus, the rib restraint horns 52 may be removed upon loading and unloading a patient onto and off of the decompression table 10. Once a patient is loaded onto the decompression table 10, rib restraint horns 52 are positioned in slider blocks 56 and hand crank 51 is manipulated to bring facing restraint horns 52 towards one another. As mentioned above, slider rail 57 is preferably in the form of an acme screw of traditional design. As hand crank 51 is mounted to slide rail 57, rotation of hand crank 51 causes slider blocks 56 to linearly translate toward or away from one another, depending upon the direction of rotation of hand crank 51.

The rib restraint horns 52 and slide rail assembly 57 are so positioned on decompression table 10 that when restraint horns 52 press against a patient's body, they are positioned to capture the lower margin of the patient's ribcage on both sides of the patient's torso. More particularly, the restraint is formed so that the base of the rib restraint preferably rests along the 12th rib and captures the end of the 11th rib, while the upper end preferably rests on the 10th rib approximately 2" from the sternum. The overall length of the padded restraint surface is preferably 8¾" long. Further, the restraint is preferably positioned at 80 degrees from the horizontal (10 degrees from vertical), toward the foot end of the table. Through the offset holes in the restraint receptacle block, the restraints are preferably positioned at 20 degrees counterclockwise from the parallel line of the length of the table. Patient-specific adjustment in relation to distance between the lower margin of the ribcage and the iliac crest is achieved through positioning of the rib restraints in the various adjustment pin holes 55 in slider blocks 56.

Lateral adjustment of the rib restraints to secure or release the ribs is achieved through the acme screw assembly. Thus, once the patient is positioned on table 10, rib restraint horns 52 are tightened against the sides of the patient's body via manipulation of hand crank 51 to securely and comfortably hold the patient's upper body to upper table section 12. This assembly thus temporarily affixes the upper portion of the patient's body to fixed upper table section 12.

Figure 7A:
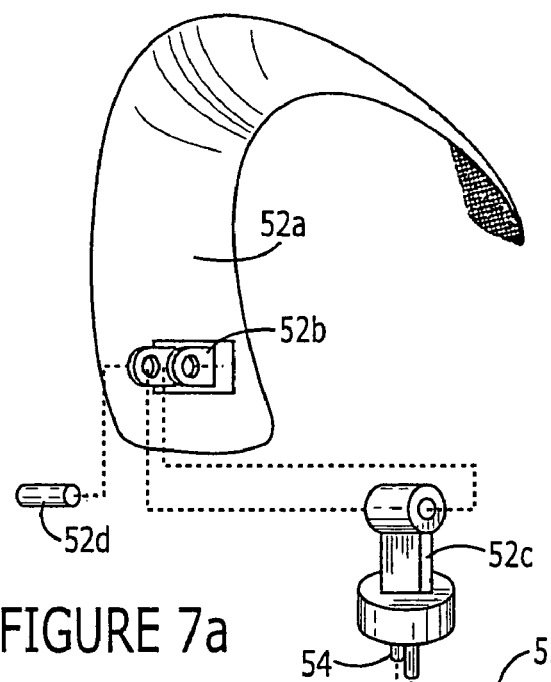
FIGS. 7a and 7b are a side exploded and front perspective view, respectively, of an alternate rib restraint system for use with the decompression table of FIG. 6.
Figure 7B:
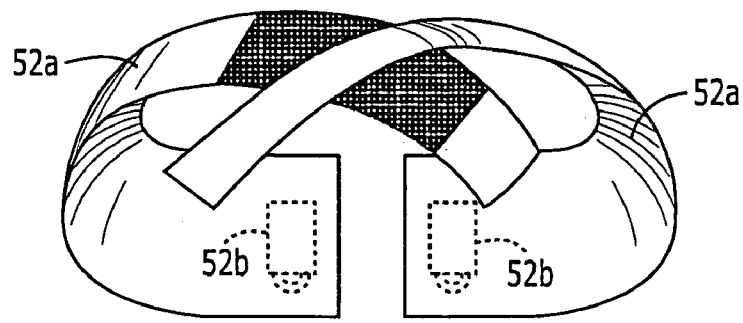

As with pelvic restraint horns 30, rib restraint horns 52 may be provided in varying sizes to ensure comfortable restraint of different sized patients. Moreover, as shown in FIGS. 7a and 7b, rigid rib restraint horns 52 may be replaced with flexible rib restraint straps 52a having facing portions of hook and loop fastening material enabling the free ends of restraint straps 52a to be temporarily secured to one another so as to wrap around and hold a patient's torso in a fixed position with respect to fixed upper table section 12. Each restraint strap 52a is likewise preferably provided a first hinge member 52b which may be removably connected to a rib harness stanchion 52c via insertion of pin 52d through both stanchion 52c and first hinge member 52b. As with the bottom of rib restraint horns 52, the rib harness stanchions 52c are preferably provided with positioning pins 54 which are configured for insertion into pin holes 55 in the top face of slider blocks 56.

Referring again to FIG. 2, also integrated with upper table section 12 is an electric infrared heating pad 18 capable of providing deep heat to paravertebral tissues during distraction. While traditional heating pads have been used that provide only topical, conductive heat that only penetrates beyond the epidermis (2–3 mm), heating pad 18 is preferably configured to produce radiant heat to depths of 25–35 mm. Heating pad 18 is thus capable of relaxing the muscles and the tissue surrounding the region of the patient's body undergoing treatment by stimulating blood flow and enhancing circulation. Integrated heating pad 18 thus enables the benefit of heat-induced muscle relaxation during the treatment session without requiring that a separate heating device be applied to the patient. Preferably, an operator may disable the integrated heating pad 18 during the treatment session in the event that the patient is uncomfortable with the heat application. As shown in FIG. 6, infrared heating pad 18 may optionally be integrated with moveable lower table section 11, for example rigidly attached to the pelvic restraint assembly, such that the heating pad moves with lower table section 11.

In a second preferred embodiment of the apparatus of the instant invention, and with particular reference to FIG. 6, the decompression table 10 may be provided with a tilting head support (shown generally at 200) which is moveable with respect to fixed upper table section 12. As with pelvic support 20, tilting head support 200 is supported on a sliding rail assembly that is attached to the actuator arm of an electric motor having a linear actuator. Operation of the motor causes the actuator arm to extend and retract, in turn moving the tilting head support 200 away from and toward fixed upper table section 12. In addition to such linear movement with respect to fixed upper table section 12, head support 200 is likewise angularly moveable so as to enable the patient's head, and thus the cervical portion of their spine, to be positioned at various angles with respect to fixed upper table section 12. As with pelvic support 20, head support 200 is preferably moveable in specific degree increments, with each specific degree of elevation corresponding to a particular cervical vertebrae or multiple cervical vertebrae intended to undergo distraction. Again, the correlation of particular angles with cervical spinal sections is believed a matter of ordinary medical skill. In order to achieve the desired tilt angle for head support 200, a separate electromechanical drive is mounted below head support 200 having an extensible arm which, when extended, pivots head support 200 about a pivot on the underside of head support 200. The angle of head support 200 may thus be varied in order to enable horizontal displacement of head support 200 to apply distraction force to specifically targeted discs in the patient's cervical spine.

As particularly shown in FIG. 6, head support 200 is preferably provided a molded concave section 201 shaped to receive the back portion of a patient's head, and is formed from a cushion material so as to maximize the patient's comfort during use. However, in order to ensure adequate and uniform application of distraction force to the cervical portion of the patient's spine, head support 200 is preferably provided a rigid base member 202 extending vertically above the bottom edge of the cushion in order to provide a rigid support to grip the base of the patient's skull during application of the distraction force. Straps 203 are likewise preferably provided having mating portions of hook and loop fastening material at their ends to wrap around the top portion of the patient's head and hold it securely to head support 200.

As particularly shown in FIG. 6, both head support 200 and pelvic support 20 may optionally be integrated in a single table 10.

Referring again to FIG. 2, both upper and lower sections 12 and 11, respectively, are positioned atop a telescoping elevator base 40 allowing the height of the top of the decompression table 10 to be adjusted for varying patients. Telescoping elevator base 40 is in turn mounted atop a frame 45 provided with castors 46 at either end enabling the entire table 10 to be moved from place to place. A hand-held electrical control 60 is preferably provided to enable a table operator to control the elevation of the decompression table 10. Control 60 is preferably attached to the table by an electrical cord and has a clip that is used to store the control on the side of decompression table 10. On the face of the control are controls enabling an operator to vary the elevation of decompression table 10. A handle 47 is preferably affixed to the table for aiding in transporting the table from place to place on castors 46, and a handle 48 is preferably provided for manually raising and lowering castors 46.

Figure 8:
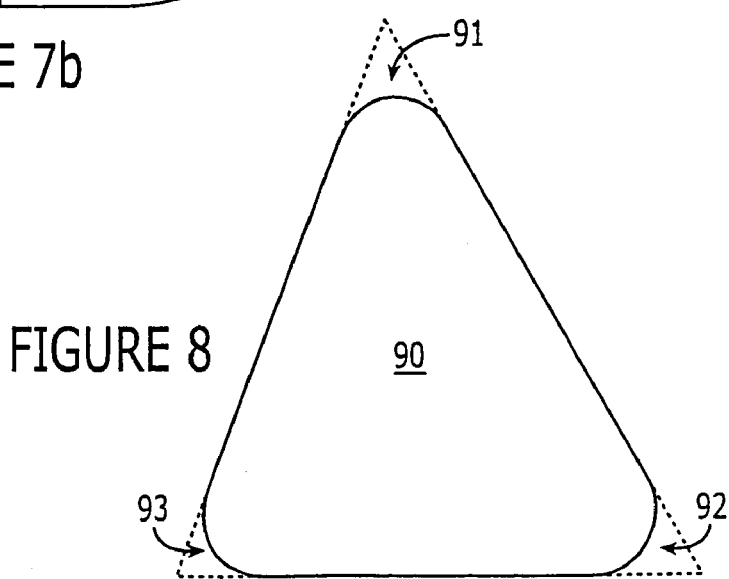
FIG. 8 is a cross-sectional view of a knee bolster for use with the table of FIGS. 2 and 6.

As shown in FIG. 8, an optional knee bolster 90 may also be provided to elevate the knees during treatment for comfort and stability of the pelvis, and is sized so that it may rest entirely on moveable lower table section 11 when in use. Preferably, knee bolster 90 is provided in the form shown in FIG. 8 which provides three separately available heights for a patient's knees. The cross-sectional view of knee bolster 90 of FIG. 8 shows a generally triangular foam pad having a first corner angle 91 of 50 degrees, a second corner angle 92 of 60 degrees, and a third corner angle 93 of 70 degrees. Each corner angle is preferably provided with a rounded corner having a minimum radius of 6 inches, and the lengths of the sides of the triangle are configured so that the height of knee bolster 90 may vary from a low setting of at least 12 inches, to an intermediate setting of at least 13 inches, to a high setting of at least 14 inches. Preferably, knee bolster 90 is constructed of high density foam, and is also preferably covered with material matching the surface of decompression table 10.

Referring again to FIG. 1, control unit 100 includes a programmable computer 101 operable with compression table 10 to control the application of the distraction force to the patient and the angle of pelvic support 20. A display unit 102 is preferably provided in communication with computer 101 to display information pertaining to the patient, progress of the treatment session, status of decompression table 10, and any other information that is pertinent to the treatment or the apparatus. Display unit 102 may be provided in the form of a touch screen control panel enabling an operator to interface with computer 101. Alternately, a computer keyboard, mouse, or other input device may alternately or supplementally be provided. A printer 103 or other output device is also preferably provided for creating a permanent written record of a patient's treatment and progress, and other reports relating to the function and status of the apparatus described herein. A modem connection port 104 is also preferably provided to enable remote monitoring, operation, update, and diagnosis of the system. In the event of a power failure, an internal battery-backup system (not shown) is also preferably provided having at least a 30 minute capacity, such battery-backup system being capable of continuing the safe operation of decompression table 10 to a controlled termination of the current treatment session, while emitting an audible warning to notify the operator of the power failure.

The operation of decompression table 10 is controlled by computer software stored on programmable computer 101. Such software controls the overall treatment process and permanently stores individual patient records. A user interacts with the software preferably via a touch-screen interface on display unit 102 (although other input devices may obviously be used) to enter data concerning the patient and parameters governing the particular patient's intended treatment.

Figure 9:
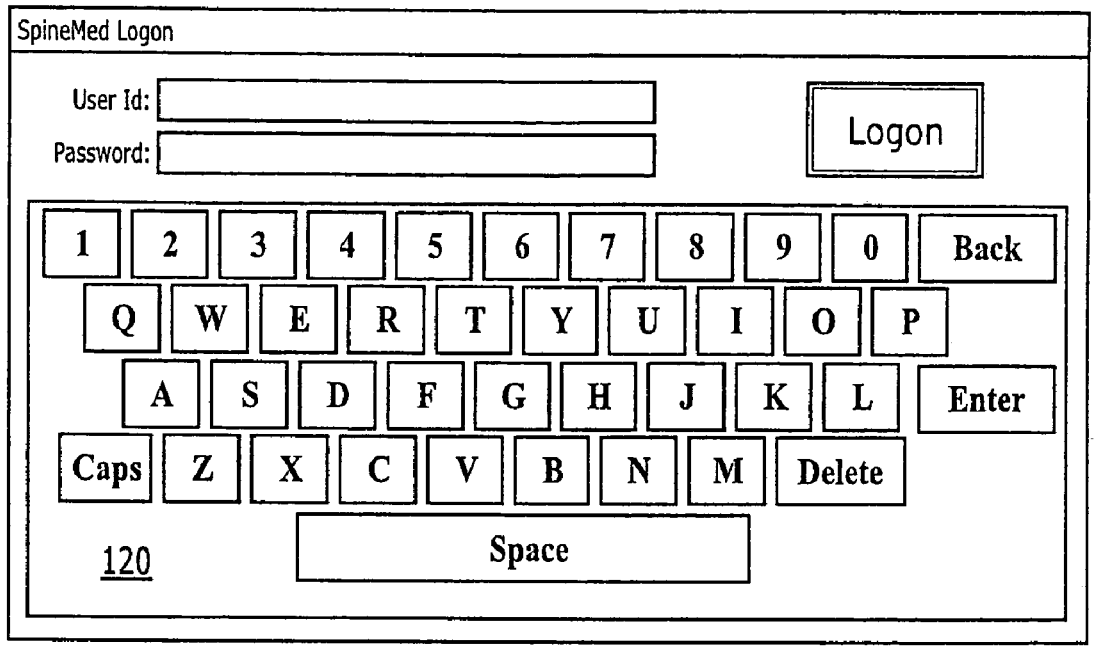
FIG. 9 is an exemplary login screen for use with the method and system of the instant invention.
Figure 10:
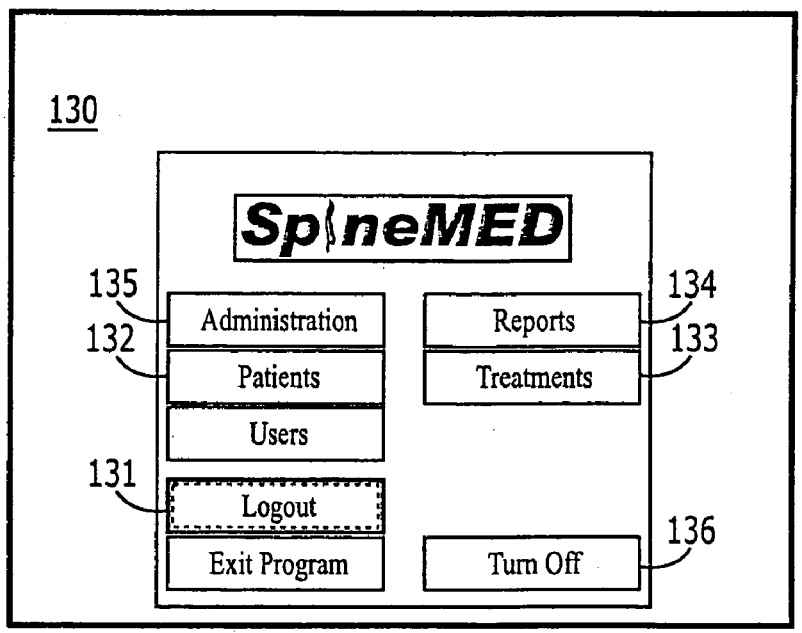
FIG. 10 is an exemplary menu screen for use with the method and system of the instant invention.

A user's first interaction with the software requires that a user provide a login identification so as to prevent unauthorized access to the software or unauthorized use of the decompression table 10. A representative login screen is depicted in FIG. 9 that prompts a user to input a unique user identification and password. Assuming that the user inputs a user identification and password that is recognized by the software (i.e., that has previously been stored in a database file listing authorized users, which database file is accessible by programmable computer 101), the user is then presented a menu screen. A representative menu screen is depicted in FIG. 10, and allows the user to access a variety of functions that may be performed by the software. For example, a logout function 131 may log the current operator off of the system without a shutdown of the software operating system. Such a function may be used to change the operator in the event of a shift change, or to enable an administrative software function (described in greater detail below). A patients function 132 may bring up a patient data screen enabling the operator to input new patient data into the system, or modify a current patient's personal data. A treatments function 133 may bring up a treatment control screen where individual treatments can be viewed or administered. A reports function 134 may bring up a report control screen which may generate a variety of patient and system reports. An administrative function 135 may bring up an administrative control screen that enables an administrator to modify information relating to the particular health clinic that operates the system. Also, a turn off function 136 may shut down the software operating system through a controlled shut down operation, as is known in the art.

An exemplary patient data screen 140 is depicted in FIG. 11, and is used to enter new patient data into the computer, and to modify existing patient's personal data. When entering new patient data, a user is preferably prompted to provide the patient's name, address, telephone number, date of birth, gender, patient identification number (e.g., a patient's social security number or other unique number), weight, an indication of whether the patient has had previous spinal surgery, the date of the patient's assessment and first treatment, the length of time the patient has had symptoms, and the patient's pathology. Preferably, multiple fields are provided in "check-box" format to indicate a particular patient's pathology, including notations for disc herniation, disc degeneration, and facet syndrome for the specific spinal regions. In the event that data is entered incorrectly (e.g., textual information is input in a field formatted to receive numeric data), the operator will be presented with an error message identifying the data entry error. Once all of the data has been properly entered, the user may save the information to store the new patient record in a database associated with a processor in programmable computer 101. Also, once the new patient record has been added and saved, the user may return to the menu screen (FIG. 10) to select another operation.

While the above description of patient data screen 140 relates to the creation of a new patient record, such patient data screen 140 may also be used to modify information in existing patient records. A user may simply select a patient in "Select Patient" field 141, at which point the software will populate the patient data screen with the particular data corresponding to the selected patient. The operator may then modify the information in individual fields on the patient data screen and save such changes as described above.

Figure 12:
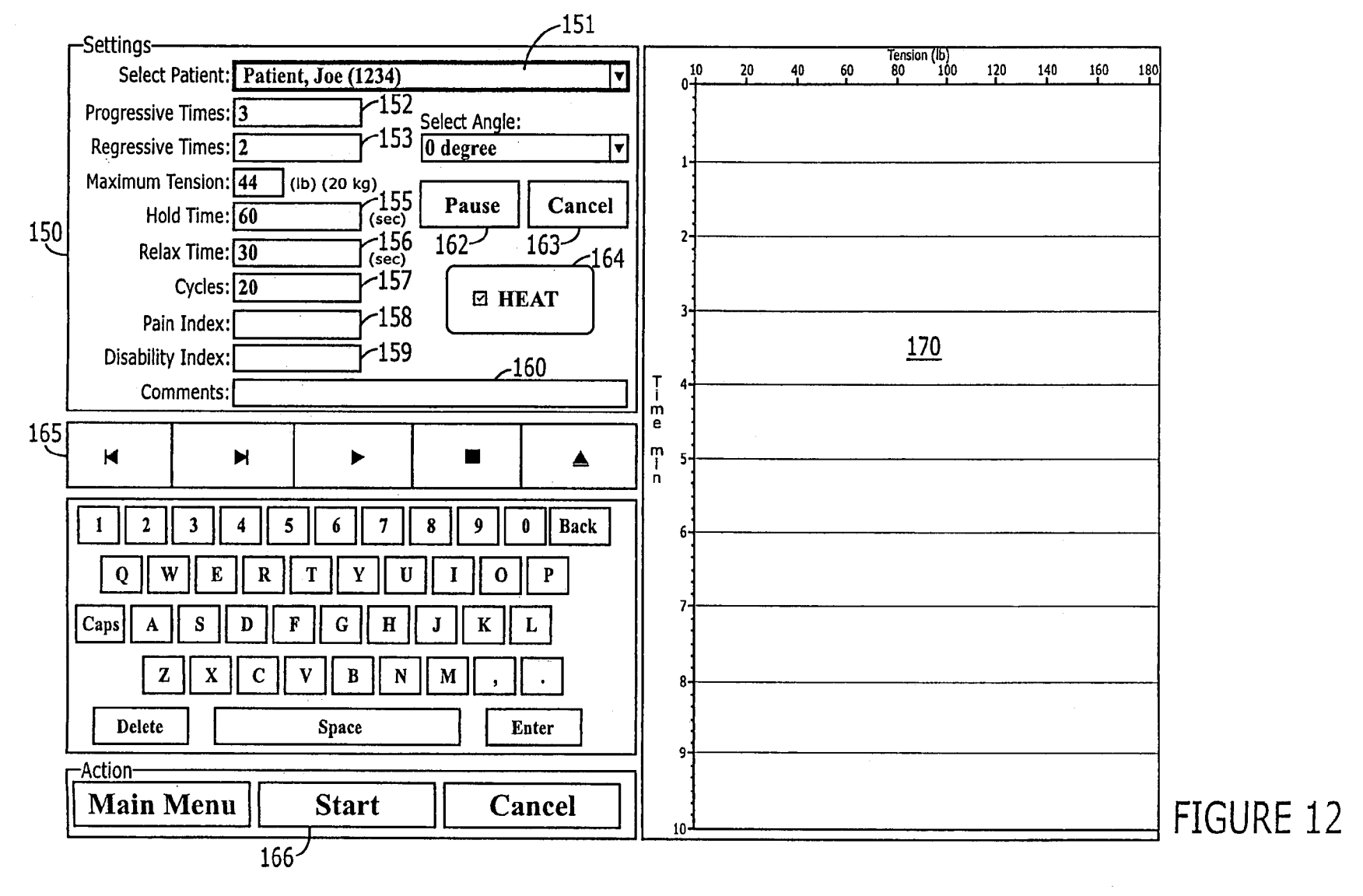

An exemplary treatment control screen 150 is depicted in FIG. 12, and may be used to enter the treatment parameters for a current treatment session and to initiate the treatment. An operator may select a patient that is to receive treatment from a "pull-down" list of patients stored in the database that is accessed through "Select Patient" field 151. Once a particular patient is selected, the software preferably populates the remaining fields with certain default values and calculated values based on the individualized patient's record.

For example, the "Progressive Times" field 152 indicates the number of cycles that the device will take to ramp up from zero tension to the maximum tension at the beginning of the treatment session. The default setting for "Progressive Times" is preferably 3 cycles.

The "Regressive Times" field 153 indicates the number of cycles that the device will take to ramp down from the maximum tension to zero tension at the end of the treatment session. The default setting for "Regressive Times" is preferably 2 cycles.

The "Maximum Tension" field 154 indicates the maximum tension that will be applied to the patient during the treatment session, and is preferably calculated by the software as follows. The maximum tension during a patient's first treatment session is ¼ of the patient's body weight minus 10 pounds. This maximum tension may be gradually increased based on the patient's response to treatment, and following a general guideline of increasing the maximum tension by 3–5 pounds/session. However, as a safety precaution, at no time will the maximum distraction tension exceed 100 pounds. While the system automatically calculates the maximum tension value for the patient's initial treatment, the operator may modify this value by simply entering the desired value in Maximum Tension field 154. The software will accept that value as long as it does not exceed the upper threshold of 100 pounds.

The "Hold Time" field 155 is indicative of the time in seconds that the maximum tension will be held during the distraction phase of the cycle, and preferably maintains a default setting of 60 seconds.

The "Relax Time" field 156 is indicative of the time in seconds that the minimum tension will be held during the relaxation phase of the cycle (as described in greater detail below), and preferably maintains a default setting of 30 seconds.

The "Cycle" field 157 is indicative of the total number of cycles to be administered during the treatment session, and preferably maintains a default value of 20 cycles. As each cycle is preferably of 90-second duration, a total treatment comprising 20 cycles will thus have a duration of 30 minutes. In the event that a treatment session must be interrupted as it is proceeding and must therefore be restarted, the value in "Cycles" field 157 may be modified to resume the treatment for the remaining period, rather than for an additional 30 minutes.

The "Pain Index" field 158 is a subjective, patient-rated pain level experienced by the patient before the treatment session begins and rated on a scale of 0 to 5 as per a Visual Analogue Scale. The Visual Analogue Scale is a color-coded card having a numerical reference on its reverse that corresponds to the patient's subjective pain index level (0–5). The patient is asked to place a point on the line that shows the level of their pain before they start the treatment. The operator then measures the line with a ruler, and the number marked by the patient is entered by the operator as data (preferably to one decimal point) in "Pain Index" field 158.

The "Disability Index" field 159 is a subjective, patient-rated disability level experienced by the patient before the treatment session begins and rated on a scale of 0 to 5 as per the Visual Analogue Scale discussed above.

The "Comments" field 160 preferably provides a text input area enabling the operator to record any observations or comments regarding the patient's response to the treatment as of the day that the current treatment session is taking place. Such comments may, for example, include an indication of the success of the treatment, the patient's response to the treatment, and any unusual occurrences during the treatment.

The "Select Angle" field 161 preferably indicates the angle at which pelvic support section 20 of lower table section 11 is to be positioned during the treatment session. The software receives this value once input by the operator, and directs the drive unit for pelvic support section 20 to change the angle of pelvic support 20 to the angle noted in "Select Angle" field 161. As discussed above, such angle may be set at any 5° step from 0° to 25° to provide localized distraction forces to only that portion of the patient's spine that is indicated as requiring treatment.

The "Pause" control 162 is preferably used to pause or interrupt the treatment session. Initiating this software function will preferably cause the software to direct the appropriate drive mechanism to stop moving lower table section 11. Initiating this software function again (when the system is paused) will resume the treatment session by directing the appropriate drive mechanism to continue moving lower table section 11.

The "Cancel" control 163 is preferably used to discontinue or permanently stop the current treatment session. Preferably, once the cancel function is initiated, the particular treatment session then underway is terminated and cannot be resumed.

A check box 164 is preferably provided to enable an operator to select whether or not infrared heat pad 18 is to be operational during the treatment session.

Optionally, an audio device such as a CD player 105 (FIG. 8) may be integrated with computer processor 101 which, along with a set of wireless headphones, will enable a patient to listen to soothing music, and thus enhance their relaxation during the treatment session. CD player controls 165 may thus also be provided on treatment control screen 150 so as to enable the operator to cause the CD player to play music during the treatment session.

Preferably, a "Start" function 166 is also accessible from treatment control screen 150 that instructs the software to begin the treatment session. Upon initiating the start function, the software preferably initiates a test of electrical safety switch 50 as follows. Immediately after initiating the start function, the software preferably displays a message to the operator instructing the operator to ask the patient to activate electrical safety switch 50. When the patient has successfully activated switch 50, the software displays a message to the operator that the switch is functioning properly, and thereafter initiates the treatment session.

Also provided on treatment control screen 150 is a trend line graph 170 which preferably records the tension applied to the patient over time throughout the treatment session. The digital image of the trend line graph is preferably stored in the individual patient data file in the database at the conclusion of the treatment session.

Figure 13:
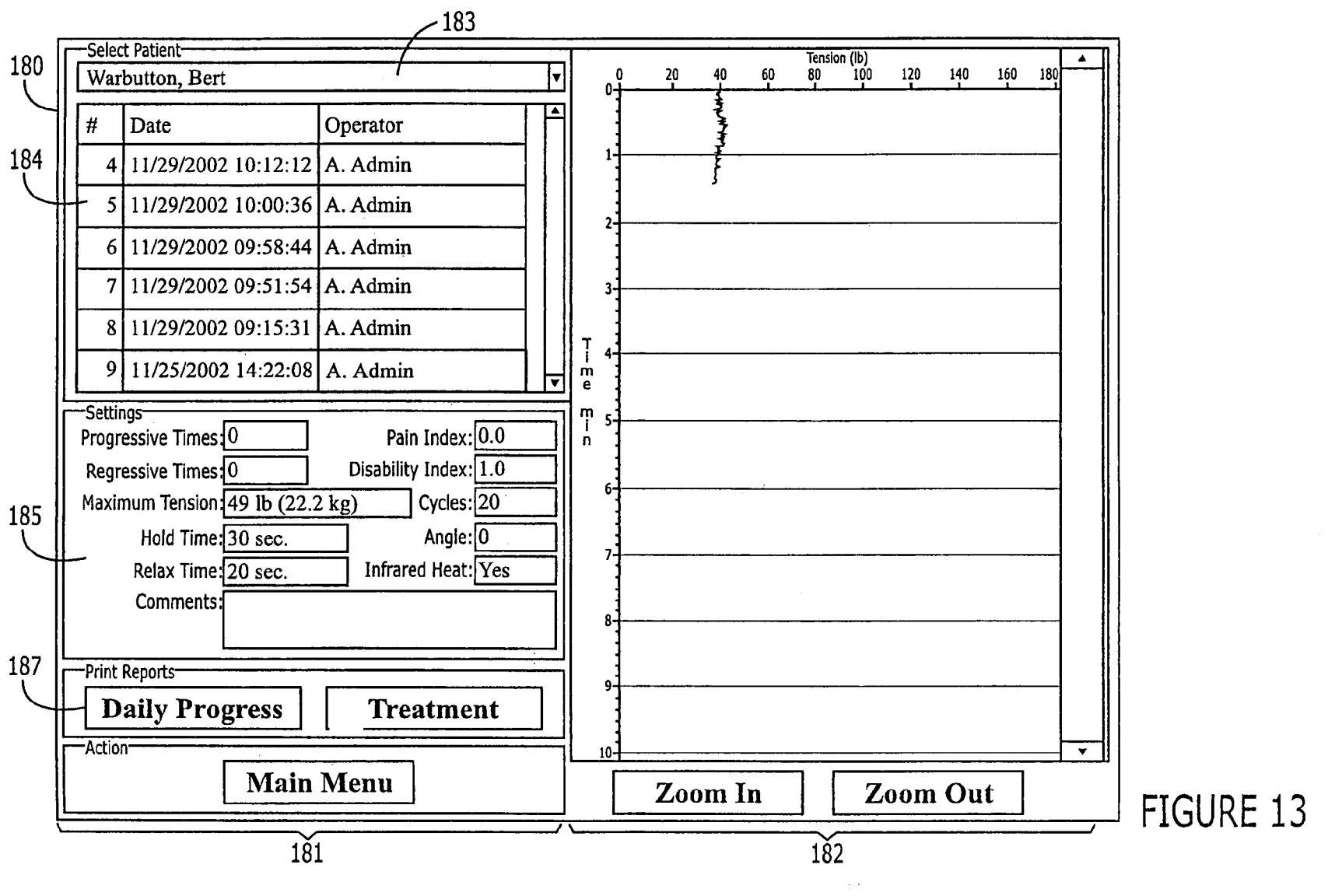

An exemplary reports control screen 180 is depicted in FIG. 13, and preferably enables an operator to search for, display, and print every patient's individual treatment session or a summary report of all treatment sessions administered to the patient. The reports control screen 180 preferably includes a first section 181 in which every treatment in the database for the selected patient may be viewed and printed, and a second section 182 in which the digital image of the trend line graph of a selected treatment is displayed. In first section 181, a "Select Patient" field 183 enables the operator to select a single patient whose records are stored in the database. Once an individual patient is selected, the software populates a treatment history chart 184 providing a listing of each treatment record associated with the selected patient. The operator may then select a particular treatment record, and the software will populate the data fields in "Settings" display 185 with the data that has been saved for the selected treatment record. Preferably, "Settings" display 185 displays "Progressive Times," "Regressive Times," "Maximum Tension," "Hold Time," "Relax Time," "Pain Index," "Disability Index," "Cycles," "Angle," "Heated Pad," and "Comments" for the selected treatment record. Likewise, second section 182 displays the completed digital trend line graph for the particularly selected treatment session. Optionally, the software may enable the operator to view the digital trend line graph at different scales via "Zoom" controls 186.

Reports control screen 180 also preferably enables an operator to cause the software to print reports of varying form. A "Daily Progress" report function 187 may be initiated by the operator which will cause the software to print out a summary of every treatment session administered to the selected patient that is stored in the database. Likewise, a "Treatment" report function 188 may be initiated by the operator which will cause the software to print a detailed report of the individual treatment currently selected, along with a printout of the trend line graph.

As mentioned above, menu screen 130 also enables an administrative function 135 which may bring up an administrative control screen which enables an administrator to modify information relating to the particular health clinic that operates the system and default values for various treatment parameters. For example, the administrative control screen may enable an operator to modify default values for progressive times, regressive times, upper limit of maximum tension, automatic calculation of minimum tension at 50% of maximum up to 50 pounds, length of time for maximum force cycle, length of time for minimum force cycle, change the force values from pounds to kilograms, and change the language preference. Access to such administrative control screen is restricted, such that initiating administrative function 135 will cause the software to query the user for an administration user identification and password. When the software receives a recognized user name and password, it displays the administrative control screen to the user, and enables the user to access the above-noted administrative functions.

A treatment session may thus be carried out as follows. Preferably, prior to loading and setting treatment parameters, the patient is fitted with the upper harness (shown in FIG. 6). The back of the harness is adjusted so that the lower arms are positioned across and below the lower margin of the ribcage, and then snugly secured. The upper portion of the harness back panel is positioned approximately at the collar level of the patient.

Using hand control 60, decompression table 10 is adjusted to the lowest vertical position for comfortable loading of the patient. If the patient will be uncomfortable from pelvic horns 30 (or for some reason is unable to use decompression table 10 in conjunction with pelvic horns 30), a pelvic belt is fitted to the patient's pelvis.

The patient is then led to decompression table 10 and instructed to sit on the edge of the table, the height of the table having been adjusted to as to enable the patient to sit on the edge of the table with the minimum amount of back flexion possible. Once the patient is sitting on the edge of the table, they are instructed to and assisted in bringing their legs up onto decompression table 10 so that the patient is in a half-sitting position. Once the patient is in the half-sitting position, the operator assists the patient in slowly reclining to a lying position.

Once the patient is lying flat on decompression table 10, the patient is slid to a position such that their iliac crests are immediately below the position of pelvic horns 30. Once the patient is positioned on the table surface so that pelvic restraint horns 30 will capture the iliac crests, the lower arms of the upper body harness (FIG. 6) are readjusted and tightened to comfortably secure the ribcage. The position of the axilla bolsters are also adjusted so that they fit comfortably within the patient's armpit. The connecting strap 89 is then attached to the mechanical safety release via buckle 17, and any slack is removed from strap 89.

Next, if the secondary pelvic restraint system is being utilized, the pelvic belt is tightened bilaterally around the patient's waist, and the left and right attachment straps of the pelvic belt are connected to the respective left and right buckles 73 and pulled tight to remove any slack. If the secondary pelvic restraint system is not being utilized, the appropriate-sized pelvic horns are inserted into their respective slider blocks 36 so that they are positioned facing one another. If necessary, the patient is repositioned such that the pelvic horns are positioned immediately above the iliac crests in the anterior superior aspect. Hand crank 31 is then manipulated to move pelvic horns 30 toward one another and the patient's iliac crests, and tightened to a comfortable but firm tension.

Optionally, knee bolster 90 is positioned under the patient's legs, and a pillow is inserted under the patient's head.

If desired, wireless audio headphones are then placed on the patient so that the patient may listen to music from audio device 105 during the treatment session.

The patient is then preferably provided electrical safety switch 50 and advised of its function and of the function of mechanical safety release lever 15.

After the patient has been thus situated on decompression table 10, the operator logs into the system to access the software stored on computer processor 101. After the operator has logged into the system, the operator may enter new patient data if the patient to be treated does not yet have a patient record stored in the database, or the operator may go directly to the treatment control screen 150 (FIG. 12) to enter the treatment parameters for the particular treatment session. Once presented with treatment control screen 150, the operator selects the particular patient from those listed in the database. The system then prompts the operator with the Max Tension Value and the angle of distraction administered during the last treatment session, which can be adjusted or altered by the operator if necessary. The operator then enters the patient's pain and disability indexes for the day, treatment comments for the day, the angle of distraction (based upon the area of the patient's spine requiring treatment), and selects whether or not to activate the infrared heat pad 18.

If desired by the patient, the operator then initiates audio device 105 and causes the software to play music from such audio device 105. The operator then causes the software to initiate the treatment session.

At the outset of the treatment session, the software causes a message to be displayed to the operator instructing them to ask the patient to activate electrical safety switch 50. Upon proper activation of electrical safety switch 50, the software causes a message to be displayed to the operator informing the operator that electrical switch 50 is functioning properly, and proceeds with the treatment session.

Typical treatment sessions would consist of a series of two force phases per cycle, which typically consist of a 60 second "Maximum Tension" distraction phase (high force), and a 30 second "Minimum Tension" relaxation phase (low force) over a modifiable number of cycles for an approximate period of 30 minutes. A graph of this operation would show a beginning force of zero pounds, which is slowly built up to the maximum force while following a linear curve. The software will gradually increase the force tensions to the preset Maximum Tension over a specific number of cycles, termed the "Progressive Times," which is preset at 3 cycles. The maximum and minimum phases in the cycles repeat through the treatment session of 30 minutes, and at the end of the session, force is gradually diminished to zero pounds over the "Regressive Times" period, which is preset at 2 cycles.

After the treatment session is completed, the operator may list additional comments on treatment control screen 180, and generate any desired reports for the treatment session.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

I claim:

1. An apparatus for treating back pain comprising:
 a fixed first body support section positioned on said apparatus so as to lie below an upper body portion of a patient's body when said patient lies supine on said apparatus;
 a moveable second body support section positioned on said apparatus so as to lie below a lower body portion of said patient's body when said patient lies supine on said apparatus, said moveable second body support section being moveable toward and away from said fixed first body support section so as to apply a distraction force to said patient's spine when said patient lies supine on said apparatus, said second body support section having a pivotable support section connected with an electro-mechanical drive, said pivotable support section positioned on said apparatus so as to lie below said patient's pelvis when said patient lies supine on said apparatus, said pivotable support section configured to pivot with respect to the remainder of said second body support section about an axis that is perpendicular to a longitudinal axis of said apparatus, said pivotable support section angularly displacing in a generally vertical direction so as to tilt said patient's pelvis and allow application of distraction forces to predetermined segments of said patient's spine upon movement of said moveable second body support section; and
 a controller, said controller further comprising computer executable code operable to (i) modify the angular orientation of said pivotable support section to isolate a desired region of a patient's spine to receive a distraction force such that a distraction force applied to said patient lying supine on said apparatus in a direction generally parallel to said patient's spine will be concentrated in said predetermined segments of said patient's spine, and (ii) cause said apparatus to cyclically apply a distraction force to said predetermined segments of said patient's spine in a direction generally parallel to said patient's spine.

2. The apparatus for treating back pain of claim 1, wherein said pivotable support section is connected with said electro-mechanical drive via an extensible actuating arm connected to a pivot on said pivotable support section.

3. The apparatus for treating back pain of claim 2, wherein said pivotable support section is moveable in selected incremental angles.

4. The apparatus for treating back pain of claim 1, said fixed first body support section further comprising a pivotable head support positioned on said apparatus so as to lie below a patient's head when said patient lies supine on said apparatus.

5. The apparatus for treating back pain of claim 1, further comprising:
 a pelvic restraint configured to affix the pelvis of a patient positioned on said apparatus to said moveable second body support section such that movement of said second body support section away from said first body support section causes movement of said patient's pelvis away from said first body support section.

6. The apparatus for treating back pain of claim 5, said pelvic restraint further comprising a plurality of pelvic horns moveable toward and away from one another.

7. The apparatus for treating back pain of claim 6, wherein said pelvic horns affix said patient's pelvis to said pivotable support section.

8. The apparatus for treating back pain of claim 6, wherein said pelvic horns are removable from said apparatus.

9. The apparatus for treating back pain of claim 8, said pelvic horns further comprising attachment means, said apparatus further comprising:
 a slider block operationally connected to a slide rail; and
 hand operated adjustment means operationally connected to said slider block, wherein said pelvic horns are attached to said slider block and said adjustment means enables movement of said pelvic horns toward and away from one another.

10. The apparatus for treating back pain of claim 9, wherein said attachment means comprises pins on said pelvic horns; and
 said slider block further comprises a plurality of holes for receiving said pins.

11. The apparatus for treating back pain of claim 6, wherein said pelvic horns are angled such that the interior face of each such pelvic horn is turned slightly toward the end of said moveable second body support section.

12. The apparatus for treating back pain of claim 6, wherein said pelvic horns are padded.

13. The apparatus for treating back pain of claim 6, wherein said pelvic horns are configured to adjustably grip against the side of a patient's body, just above said patient's iliac crests, when said patient is positioned on said apparatus.

14. The apparatus for treating back pain of claim 1, further comprising:
 a rib restraint configured to prevent movement of a torso of a patient positioned on said apparatus in the direction of movement of said moveable second section.

15. The apparatus for treating back pain of claim 14, said rib restraint further comprising a plurality of torso clamping members moveable toward and away from one another.

16. The apparatus for treating back pain of claim 15, said torso clamping members further comprising rib restraint horns positioned to engage a lower margin of a patient's ribcage when said patient lies supine on said apparatus.

17. The apparatus for treating back pain of claim 15, said torso clamping members further comprising flexible straps each of which is pivotably attached to a stanchion to engage a patient's ribcage when said patient lies supine on said apparatus.

18. The apparatus for treating back pain of claim 1, further comprising an integrated heating pad.

19. The apparatus for treating back pain of claim 18, wherein said heating pad is integrated in said fixed first body support section.

20. The apparatus for treating back pain of claim 1, further comprising a safety mechanism to enable termination of movement of said moveable second body support section away from said fixed first body support section.

21. The apparatus for treating back pain of claim 1, further comprising a knee bolster.

22. The apparatus of claim 1, wherein said pivotable support section is angularly displaced to realize an angle of 0°, 5°, 10°, 15°, 20°, and 25° and thus tilt the patient's pelvis to such degree during distraction.

23. A system for treating lower back pain comprising:
a table having a fixed first body support section positioned on said table so as to lie below an upper body portion of a patient's body when said patient lies supine on said table, and a moveable second body support section positioned on said table so as to lie below a lower body portion of said patient's body when said patient lies supine on said table, said moveable second body support section being moveable toward and away from said fixed first body support section, said second body support section having a pivotable support section connected with an electro-mechanical drive, said pivotable support section positioned on said table so as to lie below said patient's pelvis when said patient lies supine on said table, said pivotable support section configured to pivot with respect to the remainder of said second body support section about an axis that is perpendicular to a longitudinal axis of said table, said pivotable support section angularly displacing in a generally vertical direction so as to tilt said patient's pelvis and allow application of distraction forces to predetermined segments of said patient's spine upon movement of said moveable second body support section; and
a controller, said controller further comprising computer executable code operable to (i) modify the angular orientation of said pivotable support section to isolate a desired region of a patient's spine to receive a distraction force such that a distraction force applied to said patient lying supine on said table in a direction generally parallel to said patient's spine will be concentrated in said desired region, and (ii) cause said table to cyclically apply a distraction force to said desired region of said patient's spine in a direction generally parallel to said patient's spine.

24. The system of claim 23, wherein said pivotable support section is angularly displaced to realize an angle of 0°, 5°, 10°, 15°, 20°, and 25° and thus tilt the patient's pelvis to such degree during distraction.

25. The system of claim 23, wherein said table further comprises a head support.

26. The system of claim 23, wherein said table further comprises a knee bolster.

27. The system of claim 23, wherein said controller includes a display unit for interfacing a user of the table with the computer executable code.

28. The system of claim 27, wherein the display unit is a touch-screen interface.

29. An apparatus for treating back pain, comprising:
a fixed first body support section positioned on said apparatus so as to lie below an upper body portion of a patient's body when said patient lies supine on said apparatus; and
a moveable second body support section positioned on said apparatus so as to lie below a lower body portion of said patient's body when said patient lies supine on said apparatus, said moveable second body support section being moveable toward and away from said fixed first body support section so as to apply a distraction force to said patient's spine when said patient lies supine on said apparatus, said second body support section having a pivotable support section connected with an electro-mechanical drive, said pivotable support section positioned on said apparatus so as to lie below said patient's pelvis when said patient lies supine on said apparatus, the pivotable support section configured to pivot with respect to the remainder of said second body support section about an axis that is perpendicular to a longitudinal axis of said apparatus, said pivotable support section angularly displacing in a generally vertical direction so as to tilt said patient's pelvis and allow application of distraction forces to predetermined segments of said patient's spine upon movement of said moveable second body support section, said second body support section further comprising a pelvic restraint configured for affixing a patient's pelvis to said moveable second body support section such that movement of said moveable second body support section away from said fixed first body support section causes movement of said patient's pelvis away from said fixed first body support section without causing significant movement of said patient's pelvis with respect to said moveable second body support section, said pelvic restraint further comprising a plurality of pelvic horns, each said pelvic horn further comprising a base, a bracket extending upwardly from said base, and a vertically oriented pad affixed to said bracket and having a concave face opposite said bracket, said pad being positioned with respect to said apparatus such that the concavity of said pad is vertically oriented and generally faces an interior of said apparatus.

30. The apparatus of claim 29, wherein said plurality of pelvic horns are attached to said moveable second body support section so as to move in fixed relation therewith and so as to prevent movement of said pelvic horns with respect to said moveable second body support section in a direction parallel to a direction of movement of said moveable second body support section.

31. The apparatus of claim 30, said plurality of pelvic horns being attached to said moveable second body support section so as to be moveable toward and away from one another.

32. The apparatus of claim 30, said plurality of pelvic horns being removable from said apparatus.

33. The apparatus of claim 30, wherein said pelvic horns are angled such that said concave face of each of said pelvic horns is turned slightly toward the end of said moveable second body support section.

34. The apparatus of claim 30, wherein said pelvic horns are configured to adjustably grip against a side of a patient's body, just above said patient's iliac crests, when said patient is positioned on said apparatus.

35. The apparatus of claim 29, further comprising a rib restraint configured to prevent movement of a torso of a patient positioned on said apparatus in the direction of movement of said moveable second support section.

36. The apparatus of claim 35, said rib restraint further comprising a plurality of torso clamping members moveable toward and away from one another.

37. The apparatus of claim 36, said torso clamping members further comprising rib restraint horns positioned to engage a lower margin of a patient's ribcage when said patient lies supine on said apparatus.

38. The apparatus of claim 29, wherein said pivotable support section is angularly displaced to realize an angle of 0°, 5°, 10°, 15°, 20°, and 25° and thus tilt the patient's pelvis to such degree during distraction.

39. The apparatus of claim 29, further comprising a head support.

40. The apparatus of claim 29, further comprising a knee bolster.

* * * * *